United States Patent
Kärcher et al.

(10) Patent No.: US 11,744,442 B2
(45) Date of Patent: Sep. 5, 2023

(54) ENDOSCOPE, ENDOSCOPE HEAD, AND METHOD FOR CONNECTING A SHAFT TO AN ENDOSCOPE HEAD TO PRODUCE AN ENDOSCOPE

(71) Applicant: KARL STORZ SE & CO. KG, Tuttlingen (DE)

(72) Inventors: Daniel Kärcher, Radolfzell (DE); Claus Kramer, Tuttlingen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 0 days.

(21) Appl. No.: 17/672,293

(22) Filed: Feb. 15, 2022

(65) Prior Publication Data

US 2022/0167833 A1    Jun. 2, 2022

Related U.S. Application Data

(63) Continuation of application No. 15/898,614, filed on Feb. 18, 2018, now abandoned.

(30) Foreign Application Priority Data

Feb. 17, 2017   (DE) .................. 10 2017 103 267.3

(51) Int. Cl.
   *A61B 1/00*     (2006.01)
   *G02B 23/24*    (2006.01)
   *A61M 25/00*    (2006.01)

(52) U.S. Cl.
   CPC ........ *A61B 1/00073* (2013.01); *A61B 1/0011* (2013.01); *A61B 1/00066* (2013.01); *G02B 23/2476* (2013.01); *A61M 25/0014* (2013.01)

(58) Field of Classification Search
   CPC . A61B 1/00073; A61B 1/00066; A61B 1/001; A61B 1/00071; A61B 1/00128; A61B 1/00112; G02B 23/2476; A61M 25/0014; B21D 39/06; F16B 17/004; F16B 17/006; B23P 11/005; F16L 13/166
   See application file for complete search history.

(56) References Cited

U.S. PATENT DOCUMENTS

| | | | | |
|---|---|---|---|---|
| 1,951,833 A | * | 3/1934 | Maupin .................. | B21D 39/06 29/890.044 |
| 3,428,338 A | * | 2/1969 | Corwin ................ | F16L 41/001 29/523 |
| 3,837,755 A | * | 9/1974 | Benoit ...................... | F16B 7/06 29/516 |
| 4,233,726 A | * | 11/1980 | Williams .............. | F01N 13/185 29/523 |
| 4,523,872 A | * | 6/1985 | Arena ..................... | F16D 1/072 403/292 |
| 4,732,139 A | * | 3/1988 | Kawashima ............. | A61B 1/12 600/153 |

(Continued)

*Primary Examiner* — John P Leubecker
(74) *Attorney, Agent, or Firm* — McGlew and Tuttle, P.C.

(57) ABSTRACT

An endoscope includes an endoscope shaft (3), which has a cylindrical shaft tube (4), and an endoscope head (2), which is arranged at a proximal end of the endoscope shaft (3). A distal end region (11) of the endoscope head (2), has a cylindrical interior (13) with a peripheral groove (15). The shaft tube (4) is inserted into the cylindrical interior (13) and folded into the peripheral groove (15). The groove (15) is not rotationally symmetrical. An endoscope head and a method for producing an endoscope are also provided.

20 Claims, 5 Drawing Sheets

(56) References Cited

U.S. PATENT DOCUMENTS

| | | | | |
|---|---|---|---|---|
| 5,341,566 | A * | 8/1994 | Quitschau | B23P 11/005 29/890.035 |
| 5,954,637 | A * | 9/1999 | Francis | A61B 1/002 600/920 |
| 10,550,978 | B2 * | 2/2020 | Kawahara | F16L 13/146 |
| 2006/0208479 | A1 * | 9/2006 | Ozaka | F16L 41/082 29/523 |
| 2006/0236521 | A1 * | 10/2006 | Ikawa | B21D 39/06 29/523 |
| 2008/0097160 | A1 * | 4/2008 | Salvermoser | A61B 1/002 600/182 |
| 2011/0215573 | A1 * | 9/2011 | Tanaka | F01N 13/08 29/523 |
| 2013/0277955 | A1 * | 10/2013 | Wagner | F16B 17/004 29/505 |
| 2017/0028457 | A1 * | 2/2017 | Schellin | B21D 15/105 |

* cited by examiner

ENDOSCOPE, ENDOSCOPE HEAD, AND METHOD FOR CONNECTING A SHAFT TO AN ENDOSCOPE HEAD TO PRODUCE AN ENDOSCOPE

CROSS REFERENCE TO RELATED APPLICATIONS

This application is a continuation under 37 CFR 1.53(b) of pending prior U.S. patent application Ser. No. 15/898,614 filed Feb. 18, 2018, which claims the priority of German Application DE 10 2017 103 267.3, filed Feb. 17, 2017, the entire contents of each application are incorporated herein by reference.

FIELD OF THE INVENTION

The present invention relates to an endoscope with an endoscope shaft, which has a cylindrical shaft tube, and with an endoscope head, which is arranged at a proximal end of the endoscope shaft and, in a distal end region, has a cylindrical interior, wherein the shaft tube is inserted into the cylindrical interior and to a method for producing an endoscope.

BACKGROUND OF THE INVENTION

Endoscopes are used to view cavities in the human or animal body and also in technical objects. An endoscope typically comprises an elongate cylindrical endoscope shaft, which is suitable for insertion into the cavity to be viewed, and an endoscope head which is arranged at the proximal end of the endoscope shaft (i.e. the end near the user), is connected rigidly to the proximal end region of the endoscope shaft and can have attachments and control elements and also an eyepiece lens. Inside the endoscope shaft and the endoscope head there is an optical system for transmitting an endoscopic image from the distal end of the endoscope (i.e. the end remote from the observer) to the proximal end.

During their use, endoscopes are exposed to considerable mechanical and thermal stresses. There are therefore strict requirements regarding the strength of the connection between the endoscope head and the endoscope shaft. Axial forces and also transverse forces have to be able to be taken up, and a rotation of the endoscope shaft relative to the endoscope head about the longitudinal axis of the endoscope head must also be prevented.

In order to connect the endoscope shaft firmly to the endoscope head in a simple way, it is known from EP 1 872 706 A1 to push the proximal end region of an optic tube of the endoscope shaft into the distal end region of the endoscope head and to press-fit it to the latter by compression, wherein the distal end region of the endoscope head is provided on its inside with a circumferential indentation into which material of the optic tube flows with a form fit during the pressing operation. The indentation is provided as a groove extending about the full circumference, such that a particularly large amount of material can engage in the indentation and the connection of the endoscope head to the optic tube is therefore particularly stable. To prevent the optic tube from being able to rotate relative to the endoscope head about its longitudinal axis, the distal end region of the endoscope head is provided with a circumferentially limited recess into which material of the optic tube flows with a form fit during the pressing operation.

In the endoscope known from EP 1 872 706 A1, the anti-rotation effect that is achievable by the material flowing into the cavity is not always optimal. Moreover, several works steps are required for introducing the fully circumferential groove and the recess into the endoscope head, thereby increasing the manufacturing costs.

SUMMARY OF THE INVENTION

An object of the present invention is to make available an endoscope and an endoscope shaft, and also a method for producing such a endoscope, wherein the abovementioned disadvantages are avoided as far as possible.

This object is achieved by an endoscope according to the invention.

An endoscope according to the invention comprises a typically elongate endoscope shaft, and an endoscope head arranged at a proximal end of the endoscope shaft. The endoscope shaft has a substantially cylindrical shaft tube which can accommodate, for example, an objective lens for capturing an endoscopic image and an image carrier for conveying the endoscopic image to the proximal end, it being possible for these to be arranged in an inner tube extending inside the shaft tube. However, it is also possible, for example, for an electronic image-capturing device with corresponding electrical leads to be arranged in the shaft tube. Moreover, illumination light guides can extend inside the shaft tube. The shaft tube is in particular an outer tube of the endoscope shaft. The endoscope head can have an eyepiece optics unit and a proximally arranged eyepiece, or an attachment for connecting to an endoscope camera. An endoscope of this kind is also referred to as an endoscope optic and the endoscope head as an optics head. The endoscope is configured in particular as a rigid endoscope with a rigid endoscope shaft or a rigid cylindrical shaft tube.

In a distal end region, the endoscope head has an at least partially cylindrical interior into which a proximal end region of the shaft tube is inserted. For this purpose, the endoscope head can have a housing with a distal end portion which has a cylindrical or conical configuration on the outside and inside which the cylindrical interior is formed. The cylindrical interior can be a bore in the housing. The axis of the cylindrical interior is substantially coincident with a longitudinal axis of the endoscope shaft. The inner surface of the endoscope head, forming the cylindrical interior, has a peripheral groove. The groove can be formed, for example, by rotation of a corresponding tool, which generates an indentation in the surface of the cylindrical interior, and can also be designated as a fully circumferential indentation. The shaft tube is inserted with its proximal end region into the cylindrical interior and folded into the peripheral groove. This means that material of the shaft tube engages with a form fit in the groove, preferably about the entire circumference of the shaft tube, such that the shaft tube is connected to the endoscope head with form-fit engagement. The shaft tube can be press-fitted to the endoscope head, for example by compression in the longitudinal direction, and thus be folded into the groove.

According to the invention, the peripheral groove is not rotationally symmetrical with respect to an axis of the cylindrical interior, which corresponds at least approximately to a longitudinal axis of the cylindrical shaft tube inserted therein. This means in particular that the groove is formed circumferentially with a non-uniform depth and/or width and/or axial position of the groove. There is therefore at least a starting position in which the groove has a first depth and a first width and is arranged at an axial position. There is moreover at least a second circumferential position of the groove, in which the latter has a second depth and a second width and is arranged at a second axial position with respect to the axis of the interior. According to the invention, the groove is therefore configured in particular in such a way that the first depth is not equal to the second depth and/or the first width is not equal to the second width and/or the first axial position is not equal to the second axial position. The groove preferably has at least one width that corresponds to twice the wall thickness of the shaft tube in the proximal end region of the latter.

The shaft tube and the interior each have a substantially circular cross section, such that, without anti-rotation means, the endoscope shaft could rotate in relation to the endoscope head about the longitudinal axis. By virtue of the fact that the peripheral groove of the interior of the endoscope head is not rotationally symmetrical, it is possible to secure against rotation of the shaft tube inserted into the endoscope head. In particular, in a single work operation, the peripheral groove can be introduced into the inner surface of the endoscope head forming the cylindrical interior, and, by press-fitting the shaft tube to the endoscope head, a firm connection can be obtained, which at the same time secures against rotation. During press-fitting, for example by compression of the shaft tube by a sufficient amount, an outer fold of the shaft tube forms which engages with a form fit in the groove and is likewise not rotationally symmetrical. It is thus possible, by form-fit engagement, to secure particularly effectively against rotation.

The groove preferably has a non-uniform depth about the circumference, i.e. the groove has a first depth in a first circumferential position and has a second depth in a second circumferential position, wherein the first depth is greater than the second depth. The depth of the groove is in each case measured starting from an inner surface of the endoscope head forming the cylindrical interior. With respect to the axis of the cylindrical interior, the groove can extend substantially in a plane perpendicular to the axis. The fold, with which the shaft tube engages in the groove, preferably reaches as far as the bottom of the groove, in particular substantially in the entire peripheral groove or at least in a region extending across a minimum of the depth of the groove. Particularly preferably, the peripheral groove additionally has a non-uniform width about the circumference. By virtue of the fact that the groove has a non-uniform depth about the circumference, it is possible to achieve a particularly simple and effective means of preventing rotation of the shaft tube relative to the endoscope head.

A maximum depth of the groove, achieved about the circumference of the groove, is preferably about twice as great as a minimum depth of the groove. For example, the maximum depth can be approximately 0.4 mm and the minimum depth approximately 0.2 mm. Particularly reliable prevention of rotation can be achieved in this way.

The peripheral groove can advantageously be formed with a plurality of depth maxima distributed about the circumference and, preferably lying centrally between these, a plurality of depth minima Thus, in a cross section of the endoscope head, a bottom of the groove can form a closed curve in the shape of a polygon, preferably with rounded corners and curved sides. The depth maxima can each have an identical depth. Likewise, the depth minima can each have an identical depth. This permits simple production and at the same time permits a secure connection of the shaft tube to the endoscope head, wherein play of the shaft tube in the endoscope head can be avoided with increased certainty. Alternatively, provision can be made that the groove has a single depth maximum and, preferably lying opposite this, a single depth minimum.

Particularly preferably, the groove has three depth maxima arranged approximately with a spacing of 120° along the circumference, and also three depth minima arranged approximately centrally between the depth maxima. In a cross section of the endoscope head, the bottom of the groove thus constitutes a triangle-shaped curve, preferably with rounded corners and outwardly curved sides. In this way, play of the shaft tube relative to the endoscope head can be avoided particularly reliably. Alternatively, it is possible to provide two depth maxima and two depth minima, or four depth maxima and four depth minima.

In a further advantageous embodiment, the groove can be configured in such a way that, in a cross section of the endoscope shaft, i.e. in a section plane perpendicular to the axis of the cylindrical interior, a bottom of the groove forms a continuous outward curve, that is to say the bottom has peripherally a concave shape. This on the one hand permits particularly simple manufacture of the endoscope head with the peripheral groove introduced into the surface of the interior and, on the other hand, ensures that the shaft tube is folded into the groove substantially about the entire circumference and for example engages in the latter as far as the bottom of the groove about the entire circumference.

According to a preferred embodiment of the invention, the groove has a trapezoid cross section. A cross section of the groove, extending in a plane substantially perpendicular to the axis of the cylindrical interior, corresponds to a longitudinal section running through the endoscope head parallel to the axis of the cylindrical interior. A trapezoid groove allows particularly straightforward production, for example by means of a suitably guided trapezoid milling cutter, and the formation of a particularly firm connection between the shaft tube and the endoscope head.

Preferably, the inclination of the flanks of the trapezoid groove measures approximately 60° to the longitudinal axis of the cylindrical interior. More preferably, a bottom of the groove is oriented in longitudinal section parallel to the axis of the cylindrical interior and therefore parallel to the surface of the interior. The width of the bottom of the groove can be at least approximately constant in circumference, such that, with a constant angle of inclination of the flanks of the trapezoid groove, the width of the groove measured at the surface of the interior is circumferentially non-uniform, i.e. at a maximum in circumferential positions of maximum depth and at a minimum in circumferential positions of minimal depth. This not only permits particularly straightforward production but also facilitates the folding of the shaft tube into the groove upon compression.

More preferably, the shaft tube is folded into the groove in such a way that the fold of the shaft tube, i.e. the material of the shaft tube engaging in the groove, substantially fills the groove or at least touches the bottom or both flanks of a trapezoid groove. Particularly preferably, the fold substantially fills the groove in all circumferential positions or at least in circumferential regions that comprise the depth minima or extend beyond these. Depending on the process sequence, the fold with which the shaft tube engages in the groove can be a straight/vertical fold or can also be oblique to the axis of the interior or even horizontal. The shape of the fold can depend on the depth of the groove and can be non-uniform about the circumference. Thus, in circumferential positions where the groove is deeper, the fold can have a different shape than it has where the groove is shallower. For example, where the groove is deeper, the wall of the shaft tube can be less tightly folded together and fill the groove less fully than it does where the groove has a shallower depth. By virtue of the fact that the fold of the shaft tube, engaging in the groove and generated by the press-fitting, substantially fills the groove or at least touches the bottom or both flanks of the groove, rotation can be particularly reliably prevented, wherein at the same time a play of the shaft tube relative to the endoscope head can be reliably avoided.

According to a preferred embodiment of the invention, a longitudinal groove is arranged in the inner surface of the endoscope head forming the cylindrical interior, which longitudinal groove is connected to the peripheral groove and extends beyond the latter in the axial direction, wherein the longitudinal groove is deeper than the peripheral groove in the connecting region. The longitudinal groove is preferably open in the axial direction and closed in the distal direction. The longitudinal groove can also be designated as a cavity of the interior. The longitudinal groove, which opens into the peripheral groove and engages over the latter, permits the introduction of adhesive which can be drawn by capillary forces between the outer surface of the shaft tube and the inner surface of the endoscope head. The adhesive permits a liquid-tight and vapor-tight connection of the shaft tube to the endoscope head and can additionally secure against rotation. Moreover, when the shaft tube is press-fitted to the optics head, material can penetrate into the longitudinal groove, such that this likewise can provide additional securing against rotation.

An endoscope head according to the invention is configured in particular as an endoscope head for a rigid endoscope with a rigid shaft which has a rigid cylindrical shaft tube. The endoscope head has a housing which, in a distal end region, has a cylindrical interior configured to receive a proximal end region of the shaft tube. The housing of the endoscope comprises, for example, a cylindrically or conically shaped distal end portion inside which the cylindrical interior is formed. The inner surface of the endoscope head, forming the cylindrical interior, has a peripheral groove. According to the invention, the groove is not rotationally symmetrical with respect to a longitudinal axis of the cylindrical interior. It is thus easily possible to connect the shaft tube of the endoscope to the distal end region of the endoscope head by press-fitting and at the same time to secure against rotation.

In particular the groove is configured as described above, for example with a circumferentially non-uniform depth in a plane transverse to the axis of the cylindrical interior. The peripheral groove can, for example, have a trapezoid cross section with a circumferentially constant inclination of the flanks. To introduce such a groove, which has a non-uniform depth and also a non-uniform width about the circumference, into the surface of the cylindrical interior of the endoscope head, a suitably shaped milling cutter can be moved along a corresponding curve inside the interior. In addition, the interior can have a longitudinal groove which is configured as described above and which, for example, can be generated by longitudinal milling. The endoscope head is in particular an endoscope head of an endoscope configured as described above.

In a method according to the invention for producing an endoscope, a substantially cylindrical shaft tube and an endoscope head are made available, the latter having, in a distal end region, a cylindrical interior with a peripheral, non-rotationally symmetrical groove. Moreover, a proximal end region of the shaft tube is pushed into the cylindrical interior of the endoscope head, and the proximal end region of the shaft tube is press-fitted to the distal end region of the endoscope head, in particular by compression of the shaft tube. In this way, the shaft tube is folded into the peripheral groove and connected with form-fit engagement to the distal end region of the endoscope head. The production method can comprise further steps, for example the introduction of optical and/or electronic elements into the shaft tube and the endoscope head.

The press-fitting is preferably carried out by compression of the shaft tube. The shaft tube is compressed by such an amount that material of the shaft tube penetrates into the groove at least in sections, preferably about the entire circumference, and touches at least both flanks or the bottom. The press-fitting can be carried out by cold pressing.

Further features of the endoscope, of the endoscope head and of the production method are disclosed in EP 1 872 706 A1. Corresponding document US 2008/004760 A1 is in this respect incorporated by reference into the present application.

It goes without saying that the aforementioned features and the features still to be explained below can be used not only in the respectively cited combination but also in other combinations or singly, without departing from the scope of the present invention.

The present invention will be described in detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 5 is a longitudinal sectional view through a part of the housing of the endoscope head with the shaft tube pressed in;

FIG. 7 is a schematic cross-sectional view of the peripheral groove of the endoscope head with the shaft tube pressed in.

DESCRIPTION OF THE PREFERRED EMBODIMENTS

Figure 1:
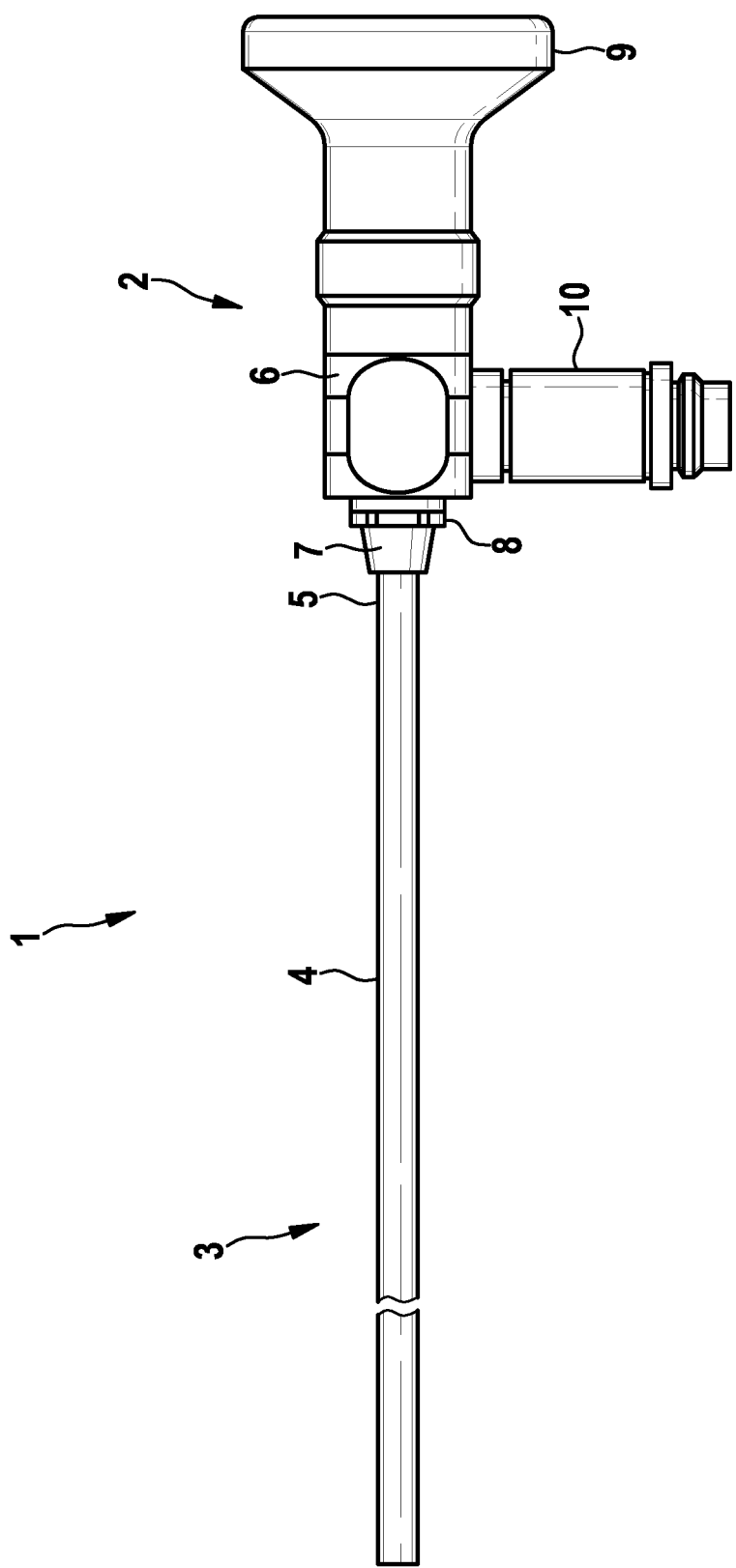
FIG. 1 is an overall view showing an illustrative embodiment of an endoscope according to the invention.

Referring to the drawings, as is shown by way of example in FIG. 1, an endoscope 1 according to the invention comprises an endoscope head 2 and an elongate endoscope shaft 3. In the endoscope 1 shown in FIG. 1, which is a rigid endoscope, the endoscope shaft 3 is of rigid configuration and has a shaft tube 4 which forms the outer tube of the endoscope shaft 3. A proximal end region 5 of the shaft tube 4 is fixedly connected to a housing 6 of the endoscope head 2. At the distal side, the housing 6 has a frustoconical surface 7 which serves for connection to the shaft of an endoscopic instrument, for which purpose a locking element 8 is moreover provided. At the proximal side, the housing carries an eyepiece 9. A light attachment piece 10 is arranged laterally on the housing 6. Optical components (not shown in the figures) are accommodated inside the endoscope. The shaft tube 4 and the housing 6 of the endoscope head 2 are produced from stainless steel, for example.

Figure 2:
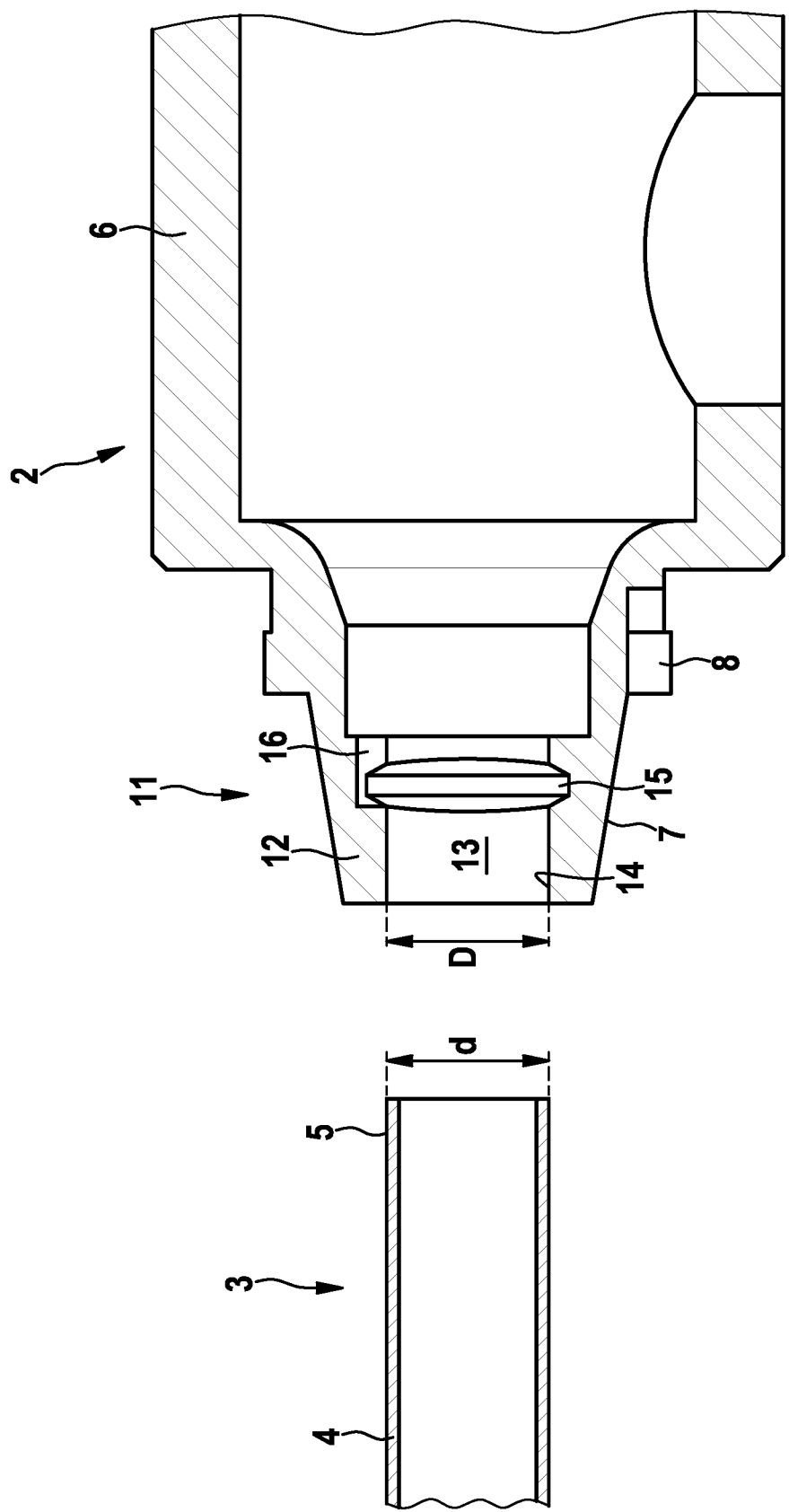
FIG. 2 is a longitudinal sectional view through a part of the housing of an endoscope head and the proximal end region of the shaft tube of the endoscope according to FIG. 1.

FIG. 2 shows the distal region of the housing 6 of the endoscope head 2 in longitudinal section. In its distal end region 11, the housing 6 of the endoscope head 2 has a cone 12, which on the outside forms the frustoconical surface 7; the cone 12 can be formed integrally with the other regions of the housing 6. On the inside, the cone 12 has a cylindrical interior 13 which extends in the axial direction and is open both at the distal side and also at the proximal side. The cylindrical interior 13 can in particular be configured as a through-bore of the cone 12. A peripheral groove 15 is introduced into the inner surface 14 of the cone 12 and extends in a plane perpendicular to the axis of the interior 13. Furthermore, a longitudinal groove 16 is introduced into the inner surface 14 of the cone 12, which longitudinal groove 16 is open at the proximal side, but closed at the distal side, and communicates with the peripheral groove 15.

FIG. 2 also shows the proximal end region 5 of the shaft tube 4 of the endoscope 1 in longitudinal section. The shaft tube 4 is cylindrical at least in the proximal end region 5. The external diameter d of the shaft tube 4 is not greater than the internal diameter D of the cone 12, preferably slightly smaller than it. The external diameter d of the shaft tube 4 can be 5 mm, for example.

Figure 3:
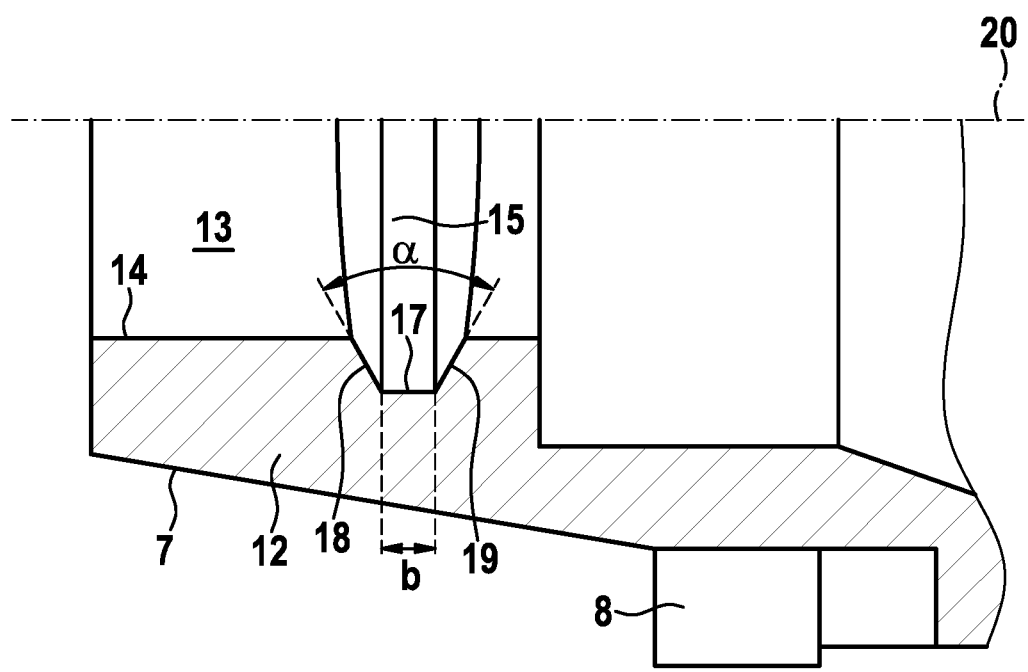
FIG. 3 is a sectional detail view showing an enlarged detail from FIG. 2.

As can be seen from FIG. 3, which shows an enlarged detail of the longitudinal section according to FIG. 2, the peripheral groove 15 has a trapezoid cross section with a bottom 17 and two oblique flanks 18, 19. The flanks 18, 19 are at an angle of α=60° to each other. In the longitudinal section shown, which shows the cross section of the groove 15, the bottom 17 extends parallel to the axis 20 of the cylindrical interior 13. The flanks 18, 19 are each at an angle of 60° to the inner surface 14 of the cone 12 and to the bottom 17 of the groove 15. In the illustrative embodiment shown, the groove 15 has a depth of 0.34 mm, and the bottom 16 has a width b=0.31 mm, in the longitudinal section plane shown.

Figure 4:
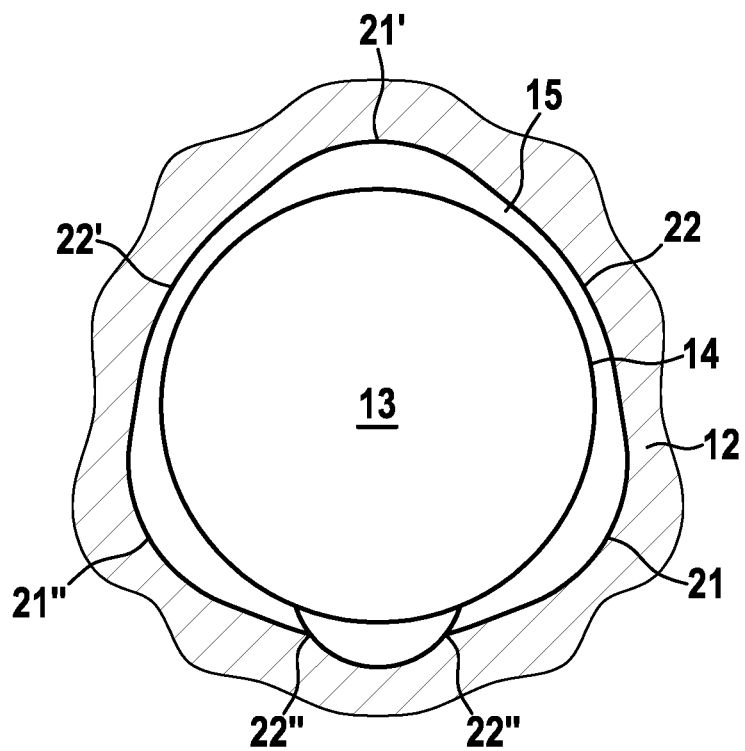
FIG. 4 is a schematic cross-sectional view showing the peripheral groove of the endoscope head.

The shape of the groove 15 is indicated in FIG. 4 in a cross section in the plane perpendicular to the axis of the interior 13 in which the groove 15 extends. As is shown in FIG. 4, the groove 15 introduced into the inner surface 14 of the cone 12 has a non-uniform depth about the circumference. In the illustrative embodiment shown, the groove 15 has three depth maxima 21, 21', 21", which are spaced apart from each other by 120° in each case and between which the depth minima 22, 22', 22" are arranged. In the cross-sectional view, the bottom of the groove 15 thus has the shape of a rounded triangle. At the position of a depth minimum 22", the longitudinal groove 16 is introduced into the inner surface 14 of the cone 12, which longitudinal groove 16 is connected to the peripheral groove 15 and engages under it, i.e. is deeper than the groove 15 in the region thereof. In the illustrative embodiment shown, the depth of the groove 15 is approximately 0.4 mm at each of the depth maxima 21, 21', 21" and approximately 0.2 mm at each of the depth minima 22, 22', 22". The cone 12 is not shown in any detail in FIG. 4.

To assemble the endoscope 1, the proximal end region 5 of the shaft tube 4 is inserted from the distal axial direction into the interior 13 until the shaft tube 4 protrudes sufficiently beyond the groove 15 in the proximal direction (see FIG. 2). The shaft tube 4 is then pressed into the distal end region 11 of the endoscope head 6. To do this, the shaft tube 4 is compressed in the axial direction, for which purpose it is, for example, clamped distally in a holding device and compressed from the proximal direction by means of an inserted mandrel. In this way, the shaft tube 4, which has a suitably small wall thickness, folds into the groove 15. The shaft tube 4 is compressed to such an extent that the material penetrating into the groove 15 substantially fills the groove 15 or, at least outside the depth minima 22, 22', 22", penetrates deeper into the groove 15 than the depth of the depth minima 22, 22', 22". For secure holding of the shaft tube 2 in the cone 12 and therefore for a firm connection of the shaft tube 2 to the endoscope head 6, it is advantageous if the material of the shaft tube 4 penetrating into the groove 15 touches at least both flanks 18, 19, and particularly advantageously also the bottom 17 of the groove 15, substantially about the entire circumference.

Figure 5:
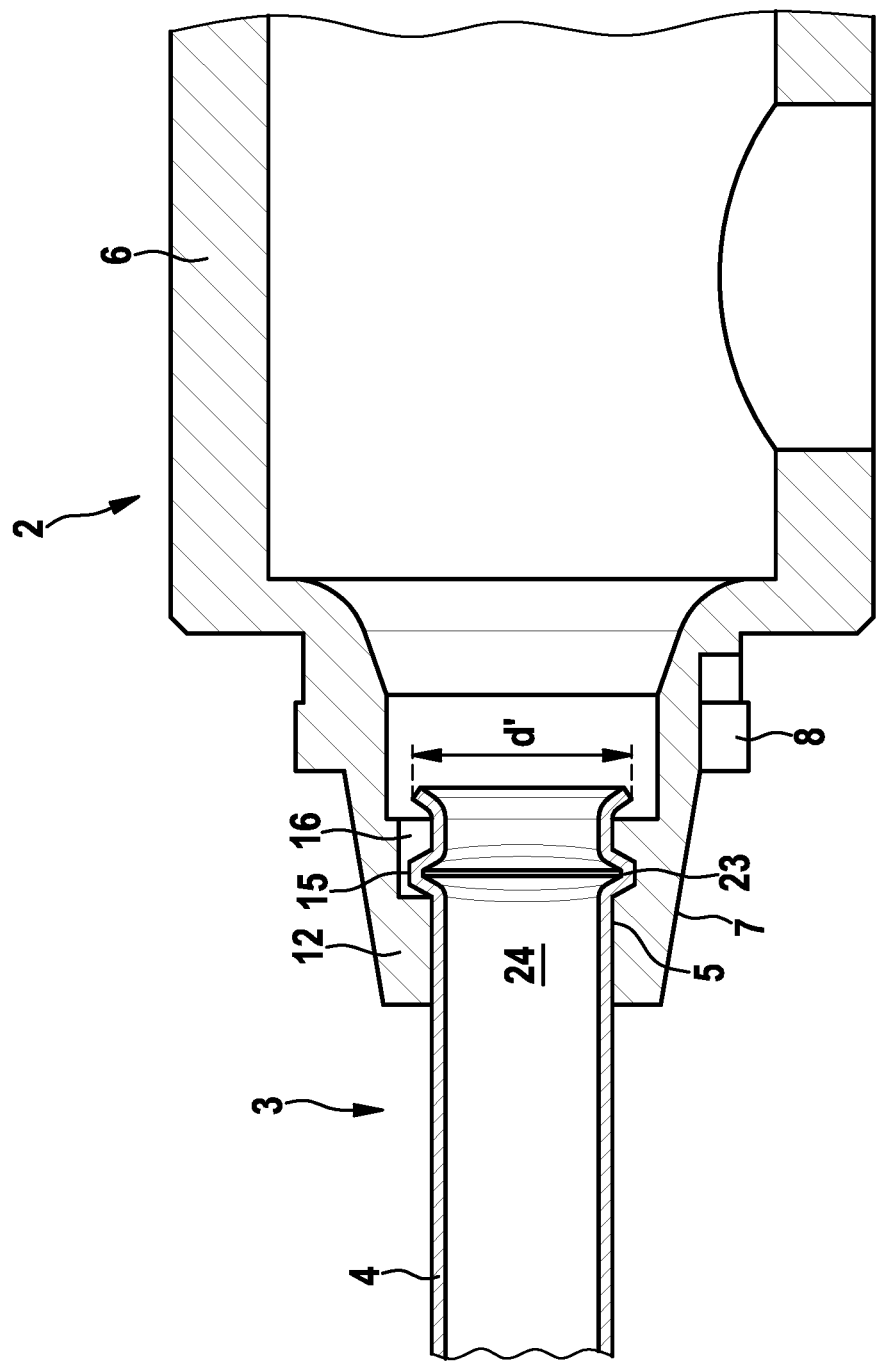
Figure 6:
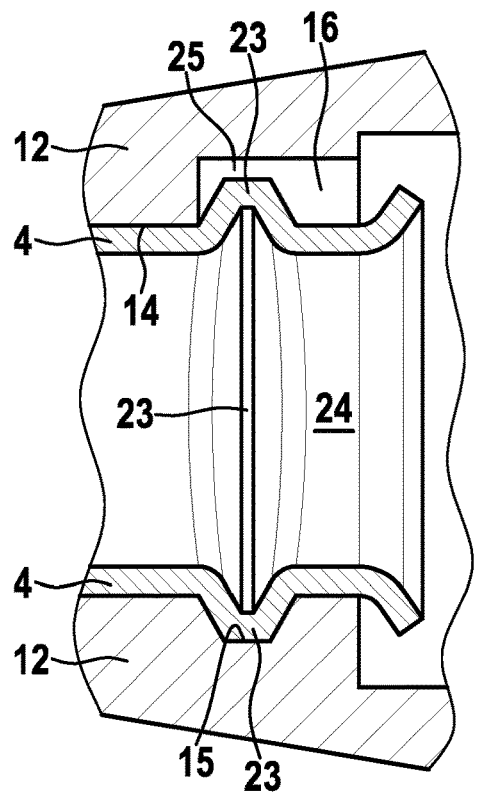
FIG. 6 is a sectional detail view showing an enlarged detail from FIG. 5.
Figure 7:
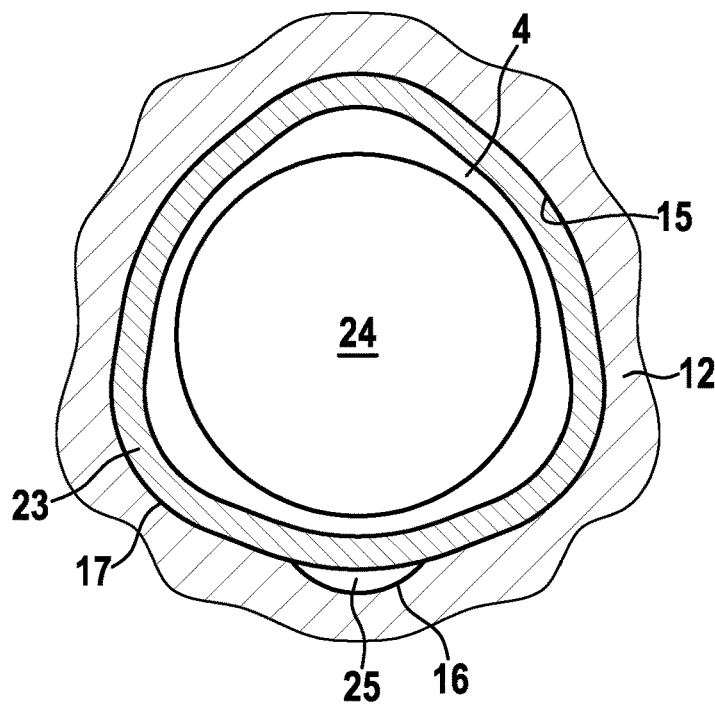

This is shown in FIGS. 5 to 7. As is shown in the longitudinal section through the distal region of the housing 6 of the endoscope head 2 in FIG. 5, the wall of the shaft tube 4 arranges itself as fold 23 in the groove 15 when compressed with a suitable tool, for example with a substantially cylindrical mandrel. The fold 23 fills the groove 15 partially or completely and thus fixes the shaft tube 4 in the cone 12. This results in a firm connection between the shaft tube 4 and the housing 6 of the endoscope head 2 and creates a cavity 24 extending all the way through the inside of the shaft tube 4 as far as the endoscope head 2. In particular, the shaft tube 4 is not only held in the cone 12 securely with respect to axial stresses and bending stresses, but also fixed against torsion about the longitudinal axis relative to the housing 6 of the endoscope head 2.

An enlarged detail of the longitudinal section according to FIG. 5 is shown in FIG. 6. As can be seen from FIG. 6, the fold 23 of the shaft tube 4 engages in the groove 15 and substantially fills the latter. The fold 23 can also penetrate into the longitudinal groove 16, although this is not essential for securing against rotation. The longitudinal groove 16 is not filled to the bottom.

This is also shown in the cross section shown in FIG. 7, which corresponds to the illustration in FIG. 4. The fold 23 fills the groove 15 about the entire circumference, including the depth maxima 21, 21', 21" and the depth minima 22, 22', 22", practically as far as the bottom. The longitudinal groove 16 is also partially filled, but not as far as the bottom, such that a space 25 remains.

In a work step following on from the compression, adhesive can be introduced into the longitudinal groove 16 from the proximal direction. This adhesive passes through the space 25 to the distal side of the fold 23 (see FIG. 6). The adhesive penetrates proximally and distally into a gap between the outside of the shaft tube 4 and the inner surface 14 of the cone 12, sets therein, and thus permits a liquid-tight and vapor-tight connection of the shaft tube 4 to the housing 6 of the endoscope head 2.

Moreover, as is indicated by the enlarged external diameter d' in FIG. 5, the shaft tube 4 can be widened in a funnel shape at the proximal end by insertion of a corresponding mandrel. Otherwise, the press-fitting of the shaft tube 4 to the distal end region of the endoscope head 2 can be carried out in the manner described in EP 1 872 706 A1.

For the sake of clarity, not all the reference signs are shown in all of the figures. Reference signs not explained in connection with one figure have the same meaning as in the other figures.

While specific embodiments of the invention have been shown and described in detail to illustrate the application of the principles of the invention, it will be understood that the invention may be embodied otherwise without departing from such principles.

What is claimed is:

1. An endoscope comprising:
   an endoscope shaft comprising a cylindrical shaft tube; and
   an endoscope head arranged at a proximal end of the endoscope shaft, the endoscope head having a cylindrical interior, in a distal end region, with a peripheral groove, wherein:
   the shaft tube is inserted into the cylindrical interior and comprises a fold;
   a bottom of the groove forms a closed, continuously concave curve;
   the groove is not rotationally symmetrical;
   the fold of the shaft tube engages the peripheral groove about the entire circumference of the shaft tube and the fold of the shaft tube substantially fills the peripheral groove;
   the cylindrical interior has a longitudinal groove connected to the peripheral groove; and
   the fold does not extend into the longitudinal groove or the fold only partially fills the longitudinal groove.

2. An endoscope according to claim 1, wherein the groove has a non-uniform depth about a circumference thereof.

3. An endoscope according to claim 2, wherein a maximum depth of the groove is about twice as great as a minimum depth of the groove.

4. An endoscope according to claim 2, wherein the groove has a plurality of depth maxima distributed uniformly about the circumference and a plurality of depth minima, wherein each of the plurality of depth minima is positioned lying between adjacent ones of the plurality of depth maxima.

5. An endoscope according to claim 4, wherein the groove has three depth maxima and three depth minima.

6. An endoscope according to claim 1, wherein the groove has a non-uniform width.

7. An endoscope according to claim 1, wherein the endoscope head has an inner endoscope head surface, the inner endoscope head surface having a first flank surface portion, a second flank surface portion and a longitudinal surface portion located between the first flank surface portion and the second flank surface portion, the longitudinal surface portion being parallel to an axis of the cylindrical interior through the endoscope head, the first flank surface portion, the second flank surface portion and the longitudinal surface portion defining a trapezoidal cross section of the groove, the shaft tube being in contact with the longitudinal surface portion, the first flank surface portion and the second flank surface portion.

8. An endoscope according to claim 1, wherein the groove has a bottom and, arranged on both sides thereof, flanks, wherein an inclination of the flanks measures approximately 60°.

9. An endoscope according to claim 1, wherein the peripheral groove is defined by an inner surface of the endoscope head, the inner surface being in contact with the fold about the entire circumference of the shaft tube.

10. An endoscope according to claim 1, wherein the cylindrical interior has a longitudinal groove connected to the peripheral groove and the longitudinal groove extends beyond the peripheral groove in an axial direction, wherein the longitudinal groove is deeper than the peripheral groove in a connecting region.

11. An endoscope comprising:
    an endoscope shaft comprising a cylindrical shaft tube; and
    an endoscope head arranged at a proximal end of the endoscope shaft, the endoscope head having a cylindrical interior in a distal end region, the endoscope head comprising an endoscope head inner surface defining a peripheral groove, the shaft tube being inserted into the cylindrical interior, the shaft tube comprising a fold, the groove having a bottom, the bottom forming a closed, continuously concave curve, wherein the groove is not rotationally symmetrical, the fold of the shaft tube engaging the inner surface about the entire circumference of the shaft tube, wherein the fold of the shaft tube substantially fills the peripheral groove about the entire circumference of the shaft tube, wherein the cylindrical interior has a longitudinal groove connected to the peripheral groove, wherein the fold does not extend into the longitudinal groove or the fold only partially fills the longitudinal groove.

12. An endoscope according to claim 11, wherein the groove has a non-uniform width.

13. An endoscope according to claim 11, wherein the endoscope head has an inner endoscope head surface, the inner endoscope head surface having a first flank surface portion, a second flank surface portion and a longitudinal surface portion located between the first flank surface portion and the second flank surface portion, the longitudinal surface portion being parallel to an axis of the cylindrical interior through the endoscope head, the first flank surface portion, the second flank surface portion and the longitudinal surface portion defining a trapezoidal cross section of the groove, the shaft tube being in contact with the longitudinal surface portion, the first flank surface portion and the second flank surface portion.

14. An endoscope according to claim 13, wherein the shaft tube is in contact with the longitudinal surface portion about the entire circumference of the shaft tube.

15. A method for producing an endoscope, the method comprising the steps of:
    providing a cylindrical shaft tube;
    providing an endoscope head with a distal end region having a cylindrical interior with a peripheral, non-rotationally symmetrical groove, wherein a bottom of the groove forms a closed, continuously concave curve;
    pushing a proximal end region of the shaft tube into the cylindrical interior of the endoscope head; and
    press fitting the proximal end region of the shaft tube to the distal end region of the endoscope head such that a fold of the shaft tube engages the peripheral groove about an entire circumference of the shaft tube and the fold of the shaft tube substantially fills the peripheral groove, wherein the cylindrical interior has a longitudinal groove connected to the peripheral groove, wherein one of the fold does not extend into the longitudinal groove and the fold only partially fills the longitudinal groove.

16. A method in accordance with claim 15, wherein the closed, continuously concave curve forms a continuous outward curve.

17. A method in accordance with claim 16, wherein the cylindrical interior comprises a central axis, at least a portion of the closed, continuously concave curve being located at a position below the central axis.

18. A method according to claim 15, wherein a non-rotationally symmetrical contour of the groove is exclusively defined by an inner surface of the endoscope head.

19. A method according to claim 15, wherein the groove has a non-uniform width.

20. A method according to claim 15, wherein the endoscope head has an inner endoscope head surface, the inner endoscope head surface having a first flank surface portion, a second flank surface portion and a longitudinal surface portion located between the first flank surface portion and the second flank surface portion, the longitudinal surface portion being parallel to an axis of the cylindrical interior through the endoscope head, the first flank surface portion, the second flank surface portion and the longitudinal surface portion defining a trapezoidal cross section of the groove, the shaft tube being in contact with the longitudinal surface portion, the first flank surface portion and the second flank surface portion.

* * * * *